United States Patent
Nadji et al.

(10) Patent No.: US 7,393,954 B2
(45) Date of Patent: Jul. 1, 2008

(54) PROCESS FOR THE PRODUCTION OF PENTOSTATIN AGLYCONE AND PENTOSTATIN

(75) Inventors: Sourena Nadji, St. Louis, MO (US); James Smoot, O'Fallon, MO (US); UmaShanker Sampath, Ballwin, MO (US)

(73) Assignee: Reliable Biopharmaceutical Corporation, St. Louis, MO (US)

( * ) Notice: Subject to any disclaimer, the term of this patent is extended or adjusted under 35 U.S.C. 154(b) by 247 days.

(21) Appl. No.: 10/734,545

(22) Filed: Dec. 12, 2003

(65) Prior Publication Data

US 2004/0181052 A1 Sep. 16, 2004

Related U.S. Application Data

(60) Provisional application No. 60/432,380, filed on Dec. 12, 2002.

(51) Int. Cl.
- C07D 491/00 (2006.01)
- C07D 513/00 (2006.01)
- C07D 515/00 (2006.01)
- C07H 19/00 (2006.01)

(52) U.S. Cl. .................. 540/568; 536/27.1; 536/27.11; 536/27.13

(58) Field of Classification Search ................ 540/568; 536/27.1, 27.11, 27.13
See application file for complete search history.

(56) References Cited

OTHER PUBLICATIONS

J. Org. Chem, Eunice Chan, et al. Total Synthesis of (8R)-3-(2-Deoxy-β-D-erythro-pentofuranosyl)-3,6,7,8-tetrahydroimidazo[4,5-$d$]1,3]diazepin-8-ol (Pentostatin), the Potent Inhibitor of Adenosine Deaminase[1a],47, 3457-3464, 1982.

J. Org. Chem, Thien Van Truong et al, "Chirospecific Synthesis of the Tetrahydroimidazodiazepinol Aglycon of Pentostatin and Its Analogues", 58, 6090-6096, 1993.

Submitted by Seiki Saito, et al., "Diethyl (2S,3R)-2-(N-tert-Butoxycarbonyl)Amino-3-Hydroxysuccinate", vol. 73, 1995.

American Chemical Society, David C. Baker, "A Total Synthesis of Pentostatin, the Potent Inhibitor of Adenosine Deaminase", 0002-7863/79/1501-6127, 1979.

J. Heterocyclic Chem, D.C. Baker et al., "Studies Related to the Total Synthesis of Pentostatin. Approaches to the Synthesis of (8R)-3,6,7,8-Tetrahydroimidazo[4,5-$d$][diazepin-8-$d$ and N-3 Alkyl Congeners (1a)", vol. 20, 629-634, 1983.

The Journal of Antibiotics, H.D. Hollis Showalter, et al., "Improved Production of Pentostatin and Identification of Fermentation Cometabolites", Vol. 45, No. 12, 1914-1918, 1982.

Drugs of the Future, Antihypertensive Calcium Channel Blocker, vol. 15, No. 7, 1990.

J. Am Chem. Soc., Kazuhiro Haraguchi, et al. "Synthesis and Characterization of Oligodeoxynucleotides Containing Formamidopyrimidine Lesions and Nonhydrolyzable Analogues", 124, 3263-3269, 2002.

American Chemical Society, Brett C. Bookser, et al., AMP Deaminase Inhibitors.2. Initial Discovery of a Non-Nucleotide Transition-State Inhibitor Series[1,], vol. 43, No. 8, 1495-1507, 2000.

J. Am. Chem. Soc., Mark D. Erion, et al., "Discovery of AMP Mimetics that Exhibit High Inhibitory Potency and Specificity for AMP Deaminase" 121, 308-319, 1999.

Nucleosides & Nucleotides, H. Jeanette Thomas, et al., "The Synthesis of Coformycin From 5-Amino-1-β-D-Ribofuranosylimidazole-4-Carboxamide", 5(4) 431-439, 1986.

Nucleosides & Nucleotides, Mikyung Hong, et al. "Irreversible, Tight-Binding Inhibition of Adenosine Deaminase By Coformycins: Inhibitor Structural Features That Contribute to the Mode of Enzyme Inhibition", 16(7-9), 1053-1057, 1997.

*Primary Examiner*—Brenda L Coleman
(74) *Attorney, Agent, or Firm*—Darby & Darby

(57) ABSTRACT

A novel, scaleable and improved process for preparing pentostatin and its analogs is disclosed. The method comprises the diastereospecific synthesis of the nucleobase from commercially available L-Dialkyl tartarates.

20 Claims, No Drawings

PROCESS FOR THE PRODUCTION OF PENTOSTATIN AGLYCONE AND PENTOSTATIN

This application claims priority under 35 U.S.C. § 119 of provisional application Ser. No. 60/432,380, filed Dec. 12, 2002, which is incorporated by reference in its entirety.

FIELD OF INVENTION

A novel, scaleable and improved process for preparing pentostatin aglycone, and pentostatin is disclosed.

BACKGROUND OF THE INVENTION

Pentostatin and coformycin are tight-binding naturally occurring inhibitors of Adenosine Deaminase (ADA) with a $K_i$ of $2.5 \times 10^{-12}$ M and $1.0 \times 10^{-11}$ M, respectively (Drug of the future, vol. 15, No. 7, 1990). As expected, Pentostatin greatly enhances the antiviral activity of vidarabine (Ara-A) (Sloan, B. J.; J. K. Kielty & F. A. Miller, Ann. N. Y. Acad. Sci. 284:60-80, 1977.) In later studies, Pentostatin has been found to be effective against chronic lymphocytic leukemia (Kef ford, R. F. & R. M. Fox, Br. J. Haemto. 50: 627-636, 1982; Ho. A. D.; J. Thaler, P. Stryckmans, B. Coiffier, M. Luciani, P. Sonneveld, K. Lechner, S. Rodenhuis, R. Zittoun, J. Natl. Cancer Inst., 82: 1416-1420, 1990) and hairy cell leukemia (O'Dwyer, P. J.; S. Marsoni, M. T. Alonso, & R. E. Wittes, Cancer Treatment Symp. 2: 1-5, 1984; Spiers, A. S. D.; J. C. Ruckdeschel & J. Horton; Scand. J. Haematol, 32: 130-134 1984). Indeed, Pentostatin (Nipent) is now an approved and highly effective agent for the treatment of interferon-refractory hairy cell leukemia (Drug of the future, vol. 15, No. 7, 1990; Cassileth, P. J.; B. Chuvart, A. S. D. Spiers, D E. P. Harrington, F. J. Commings, R. S. Nieman, J. M. Bennett & M. J. O'Connell: J. Clin. Oncol.; 0.9: 243-246, 1991.) Coformycins analogs have attracted more attention in recent years because the inhibitors of AMPDA (Adenosine monophosphate deaminase) may present site- and event-specific drugs that could prevent or attenuate ischemic tissue damage resulting from a stroke or a heart attack (Erion, Mark D.; S. R. Kasibhata, B. C. Bookser, P. D. Van Poelje, M. Rami Reddy, H. E. Gruber & J U. R. Appleman: J. Am. Chem. Soc., 121, 308-319, 1990.)

Two additional analogs with similar activity have been isolated and characterized. They are the 2'-chloro-2'-deoxy compound adechlorine and a carbocyclic analog adecypenol (Tanaka, H.; T. Kawakami, Z. B. Yang, K. Komiyama, S. J. Omura: J. Antibiot., 42, 1722, 1989; Omura, S; H. Tanaka, N. Imamura: J. Antibiot. 39; 309, 1986.)

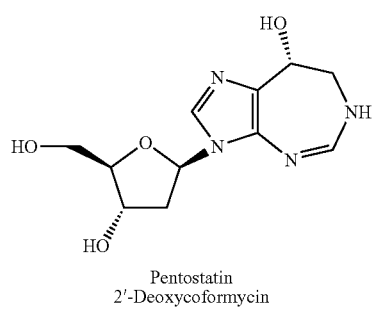

Pentostatin
2'-Deoxycoformycin

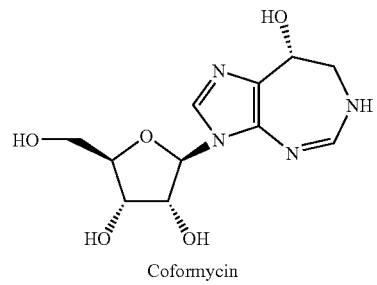

Coformycin

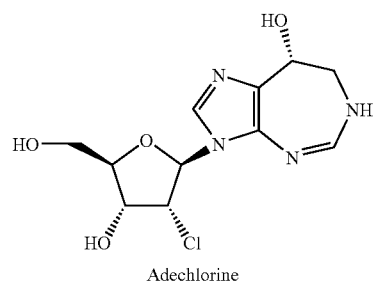

Adechlorine

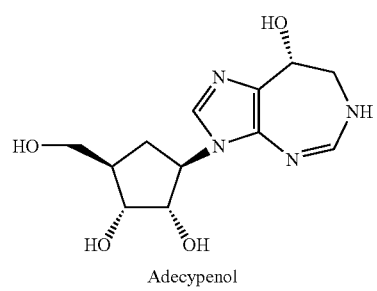

Adecypenol

Due to a wide range of therapeutic applications of coformycins, one can expect demand for the production of these drugs to increase from 500-1000 g/year to multiple kilograms per year.

Pentostatin is currently being produced commercially by large-scale isolation from the fermentation beer of *streptomyces antibiticus* NRRL 3238 according the procedure that was developed by Showalter-McDonnell-Edmunds at Park-Davis Pharmaceutical, Warner-Lambert Co. (Dion, H. W.; P. W. K. Woo & A. Ryder, Ann. N. Y. Acad. Sci. 284; 21-29, 1977; Woo. P. W. K.; H. W. Dion. S. M. Lang, L. F. Dahl & L. J. Durham, J. Heterocycl. Chem. 11: 641-645, 1974.) The fermentation produces other UV-absorbing contaminations. The major contaminant is the (8S)-isomer (1.1%). 2'-deoxyguanosine is another minor component originally identified in the fermentation beer (Showalter H. D. H., Bunge, R. H., French, J. C., Hurley, T. P., Leeds, R. L., Leya, R., McDonnell, P. D., Edmunds, C. R., J. Antibiotics, 45, 1914-1918, 1992)

Warner-Lambert researchers were also the first to report the complete synthesis of Pentostatin. Their synthetic route is shown in scheme (I).

Scheme I

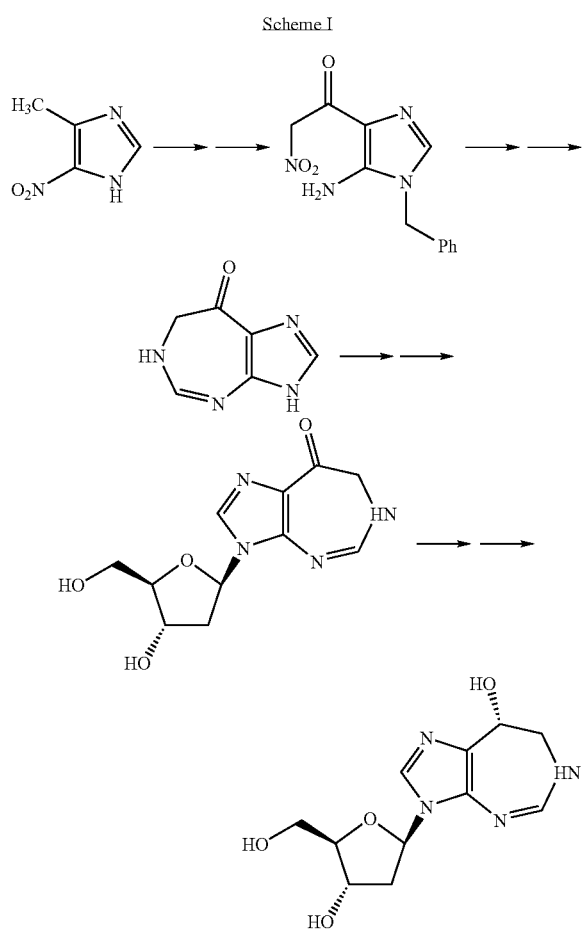

The earlier synthesis contained total 11 steps and overall yield of 1.6% (Baker, D. C.; S. R. Putt, J. Am. Chem. Soc. 101, 6127-6128, 1979). This involved the synthesis of a five-and seven-membered fused heterocyclic ring aglycone, followed by low-yield glycosylation and reduction of the ketone functionality to produce the 8-R and 8-S isomers. In the following years the Warner-Lambert researchers modified the glycosylation step and obtained 51% of the desired isomer (beta-isomer) and made improvements on other steps. However, the isolation of Pentostatin from the fermentation beer remains to be the only viable preparative method (Chan, E.; S. R. Putt, H. D. H. Showalter, & D. C. Baker, J. Org. Chem. 47: 3457-3464, 1982; Showalter, H. D. H.; S. R. Putt, P. E. Borondy & J. L. Shillis, J. Med. Chem. 26: 1478-1482, 1983).

Other schemes have been reported in the literature. Ohno et al. focus their work on the photo-assisted ring-expansion of nebularine and produced the coformycin in overall yield of 30%. Thier scheme, depicted below, is short and exclusively produces the desired 8-R stereoisomers (Ohno, M.; N. Yagisawa, S. Shibahara, S. Kondo, K. Maeda & H. Umwzawa, J. Am. Chem. Soc. 97, 4326-4327, 1975). However, experiments indicate that the scheme is not applicable to the corresponding deoxy isomer and a much lower yield and extensive decomposition is observed.

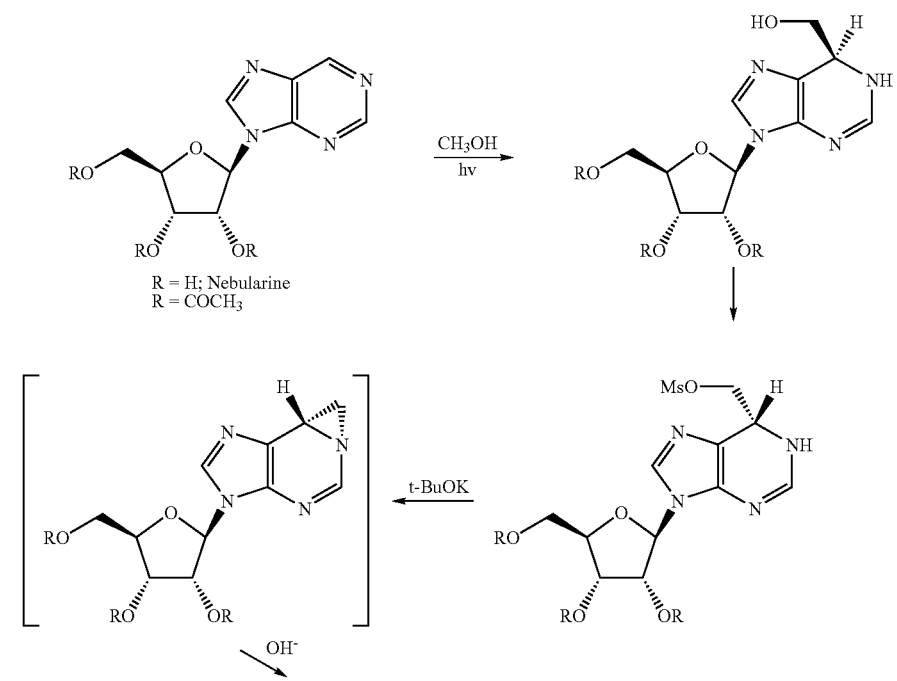

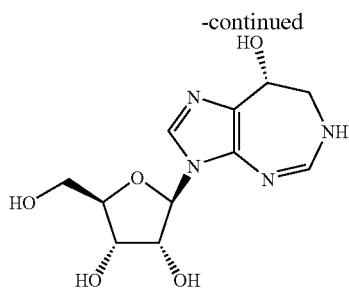

A few years later, another method was reported by Rapoport's laboratory at the Berkeley (Truong, T. V. T. & H. Rapoport, J. Org. Chem.: 58, 6090-6096, 1993). As a starting material they used L-vinylglycine which was prepared in three steps from L-methionine methyl ester hydrochloride with a 60% yield (Carrasco, M.; R. J. Jones, S. Kamel, T. Truong, & H. Rapoport; Org. Synth. 70: 29-34, 1991). The exchange of the CBZ protective group with the BOC group was found to be important for separation of syn- and anti-epoxide by flash chromatography (Truong, T. V. T. & H. Rapoport, J. Org. Chem.: 58, 6090-6096, 1993).

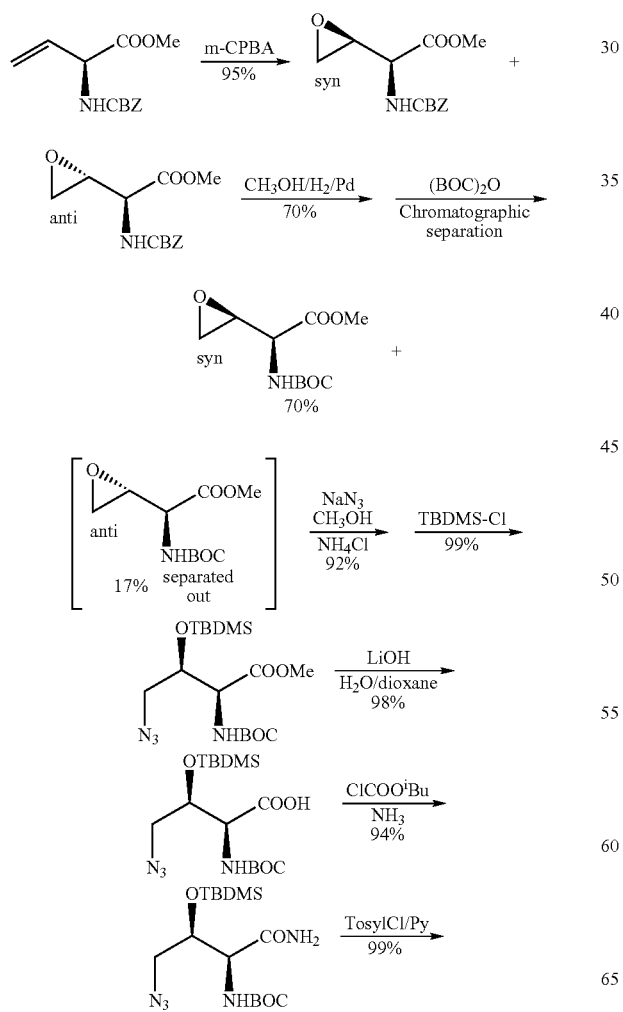

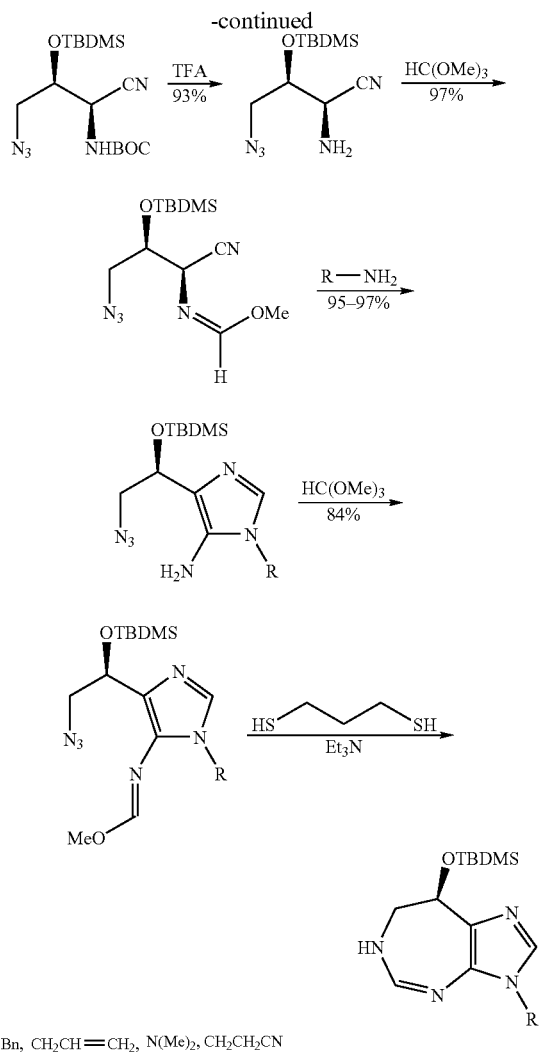

R = Bn, $CH_2CH=CH_2$, $N(Me)_2$, $CH_2CH_2CN$

As the above scheme shows, using L-vinylglycine as a chiral starting material, the Berkeley researchers have achieved a high yield stereo- and regiospecific synthesis of various protected, enantiomerically pure Pentostatin aglycone. However, none of the intermediates are commercially available and the total 16 synthetic steps make this protocol less desirable for the large-scale production of Pentostatin.

Other synthetic methods reported by Hosmane (Hong, M., Hosmane, R. S., Nucleosides & Nucleotides, 16, 1053-1057, 1997) are represented below:

Ramachandra S Hosmane et al. synthesis

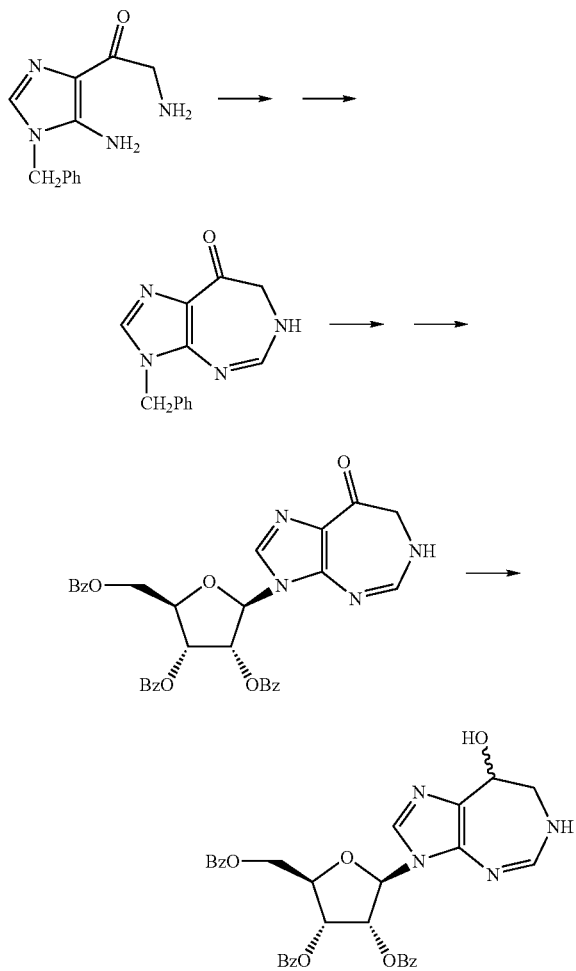

A synthesis by Montgomery (Thomas, H. J.; J. M. Riordan & J. A. Montgomery, Nucleosides & Nucleotides, 5: 431-439, 1986) is represented below:

Coformycin synthesis by Thomas, Riordan & Montgomery

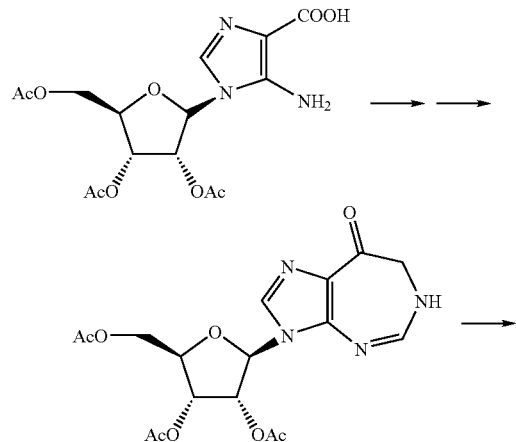

-continued

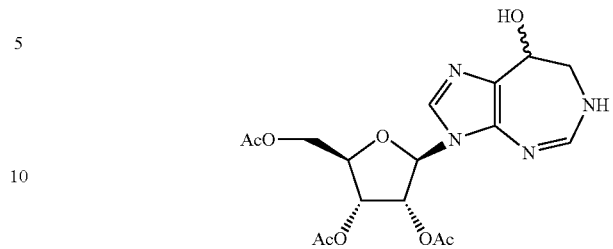

These two methods are not desirable for scale-up because they involve either glycosylation with a moderate beta/alpha [β/α] ratio or generation of the $C_8$-hydroxy with the correct stereochemistry at a very late stage of the synthesis, which results in appreciable loss of yield (usually about 40%, see the above scheme).

There are also several reasons for finding an alternative synthetic route to the current enzymatic process of producing Pentostatin.

The major steps used in the original isolation of Pentostatin involved a carbon adsorption/desorption procedure followed by chromatography on Darco G-60 and then on Sephadex G-10. The course of the fractionation was monitored by testing fractions for their ability to inhibit the deamination of adenosine by ADA. Repeated re-crystallization of the product from the final, most active chromatographic fractions afforded less than 8 g of Pentostatin from 9,500 liters of beer. The low yield and considerable labor involved in isolating Pentostatin using this procedure are not practical for the production of kilogram lots of the drug. An alternative process, coupled with a rapid HPLC method for assaying Pentostatin, was later developed. The improved process yielded 648.5 g of >99.7% pure Pentostatin from 50,000 liter of fermentation beer. However, the scale-up difficulties, the number of contaminants and the labor involved remained to be challenging to tackle. Other processes more or less yield the same amounts of the active drug using other fermentation and purification procedures (Kusakabe, H; K. Kodma, H. Machida, Y. Midorikawa, A. Kuninanka & H. Yoshino; Jap. Kokai, 52128292, 1977; JP 5230991, 1977; Omura, S.; H. Tanaka & N. Imamura.: 2'-deoxycoformycin by actinomadura; Jap. 61289896, 1986.).

The enzymatic process, apart from involving considerable labor, suffers from the fact that it still is a biochemical process and several nucleoside contaminations are produced during the fermentation. This poses the challenge to identify and remove them efficiently from the final product. Identified nucleoside contaminations are: coformycin, Ara A, deoxyguanosine, the (8S)-isomer, 8-ketodeoxy- and 8-keto-coformycin (Hanvey, J. C.; E. S. Hawkins, D. C. Baker, R. J. Suhadolink, Biochemistry, 27: 5790-5795 (1988). Separation of these contaminates requires special techniques and expertise. For example a recent patent describes the efficient separation of coformycin, formycin A and isoformycin using CG-50 column and a special elution procedure for separation of coformycin from nucleosides occurring with it (see Fr Pat. 2383966, 1978).

There is a demand for much higher quantities of Pentostatin (Bookser, B. C.; S. Rao Kasibhatla, J. R. Appelman & M. D. Erion, J. Med. Chem. 43: 1495-1507, 2000) and current methods do not comfortably produce such amounts. Thus, a practical, scalable, concise and free from hard-to-separate contaminants that could produce Pentostatin at a competitive price is most desirable at this time. None of the reported synthetic schemes can satisfy all of these requirements.

SUMMARY OF INVENTION

This invention relates to a short, novel and scaleable synthetic route to Pentostatin, pentostatin analogs and the pentostatin aglycone (which is the 5:7 ring system also known as the nucleobases), and is based on low-cost, and commercially available Dialkyl-L-Tartarate starting materials. When R is a carbohydrate such as deoxyribose then the final product formed is the nucleoside drug pentostatin 1a. If R is a removable protecting group then it leads to the synthesis of pentostatin aglycone—an intermediate suitable for glycosylation to give Pentostatin 1a.

Pentostatin, a pentostatin analog, a pentostatin aglycone, or a pentostatin aglycone analog is synthesizing by a method which comprises the steps of converting a dialkyl tartarate to a succinonitrile derivative; reacting the succinonitrile derivative with an amine to form a substituted imidazole compound, wherein the substituted imidazole compound comprises a moiety having a cyano group; reducing the cyano group on the substituted imidazole to a primary amino group; and cyclizing the primary amino group with a second amino group on the substituted imidazole compound to obtain pentostatin, pentostatin analog, pentostatin aglycone, or pentostatin aglycone analog.

One embodiment of the invention involves the preparation of pentostatin which is shown here in which R is the deoxyribose moiety:

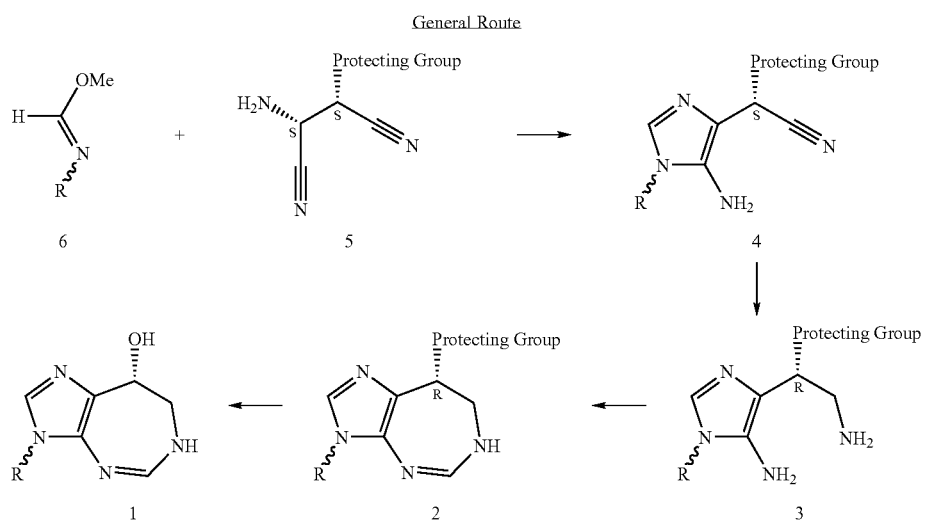

The R groups could be carbohydrate moieties, alkyl groups, alkenyl, aryl, aryl-alkyl with various substituents. Examples of protecting groups include OTBDMS, and OT-ButPh$_2$Si.

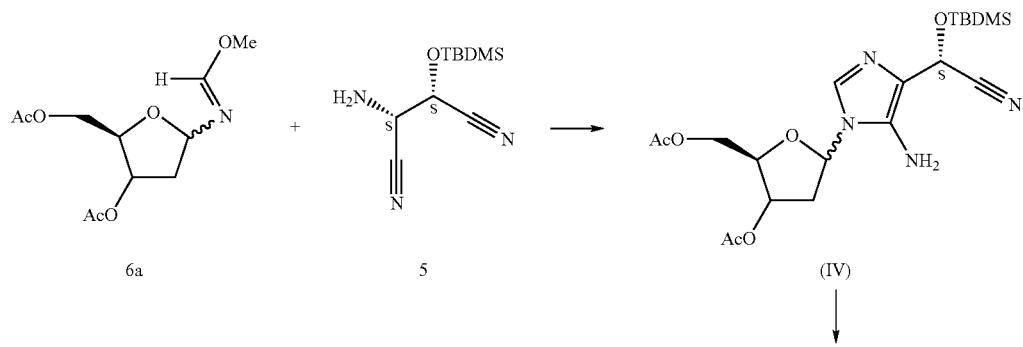

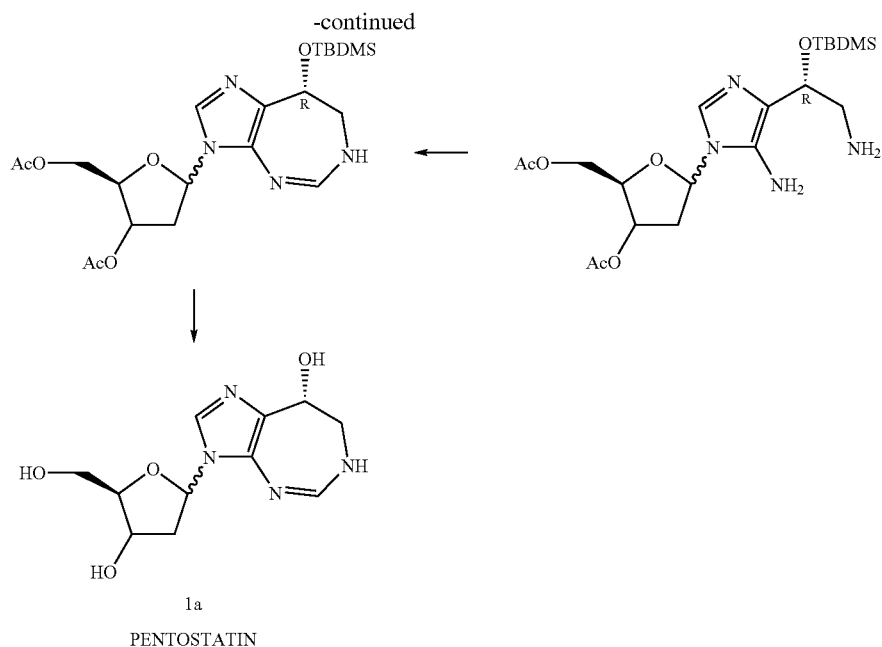

1a
PENTOSTATIN

Pentostatin is synthesized by a method which comprises the steps of: converting a L diethyl tartrate to a succinonitrile intermediate, the intermediate having the formula:

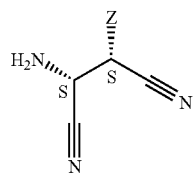

wherein Z is OR, wherein R is a protecting group; reacting the succinonitrile intermediate with an amino sugar intermediate having the formula:

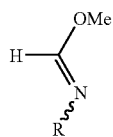

wherein R is

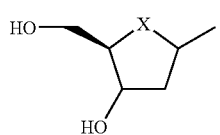

wherein X is O, S, NH, or $CH_2$; or

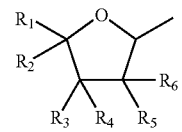

wherein $R_1$, $R_2$, $R_3$, $R_4$, $R_5$, and $R_6$ are independently selected from OH, H, methyl, alkyl, $CH_2OH$, or a halogen; or

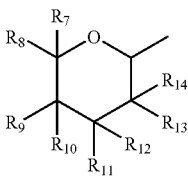

wherein $R_7$, $R_8$, $R_9$, $R_{10}$, $R_{11}$, $R_{12}$, $R_{13}$, and $R_{14}$ are independently selected from OH, H, methyl, alkyl, $CH_2OH$, or a halogen, wherein the substituted imidazole compound comprises a moiety having a cyano group; reducing the cyano group on the substituted imidazole to a primary amino group; and adding a orthoformate to cyclize the primary amino group with a second amino group on the substituted imidazole compound; and removing the protecting group to obtain pentostatin or the pentostatin analog.

DETAILED DESCRIPTION OF INVENTION

The two key starting materials for the synthesis of Pentostatin (shown above as 5 and the imino ether derivative 6a) are prepared as follows.

The succinonitrile (dinitrile) derivative (5) is made from a Dialkyl L-Tartarate, (for e.g. L-Diethyl tartarate), as the chiral synthon because it is a low-cost optically active 4-carbon building block unit that posseses the correct stereo configuration that eventually will become the (R)-8-hydroxy group of the target molecule, pentostatin. Futher, they possess a $C_2$-symmetry that makes the separation of the diastereomeric intermediates less problematic (Mori, K.; H. Iwasawa, Tetrahedron, 36: 87-90, 1980.). Dialkyl L-Tartarates can be obtained from Aldrich Chemical, See e.g., Cat# 15,684-1 and Cat# 16,345-7).

C$_2$-symmetrical diethyl tartarate has been used in the preparation of optically active β-hydroxy-α-amino acids. These classes of compounds are important not only as peptide building blocks but also as precursors to many amino-hydroxy antibiotics and amino sugars (Mori, K.; H. Iwasawa, Tetrahedron, 36: 87-90, 1980). The procedure published by Saito-Komada-Moriwake is the most practical and amenable to large-scale preparation.

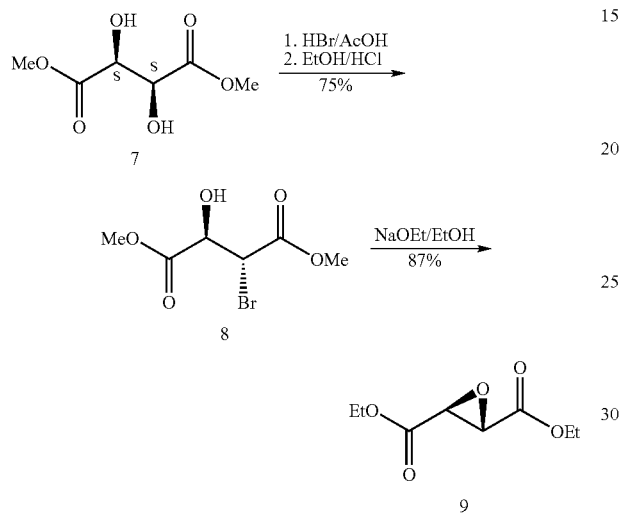

The synthetic route shown above involves bromination of diethyl L-tartarate to diethyl (2S,3S)-2-bromo-3-hydroxy succinate (Saito, S.; K. Komada & T. Moriwake. Org. Synth. 73: 184-200, 1995), and conversion of the latter to diethyl (2R,3R)-2,3-epoxysuccinate. The nucleophilic cleavage of the epoxide and amidation of the ester moieties by ammonia and finally the protection of the amino group to the N-(tert-butoxycarbonyl) amino group. The silylation of the free hydroxyl is carried out with TBDMS-Cl:

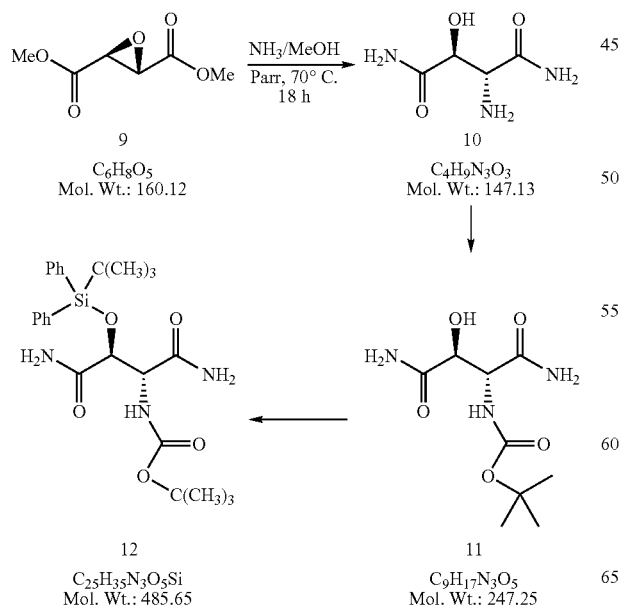

The diamide silyl ether is dehydrated by conversion of the hydroxyl to tosyl group and elimination to form the dinitrile. Finally the t-boc group is deprotected to give the aminosilylether-dinitrile (see scheme below)

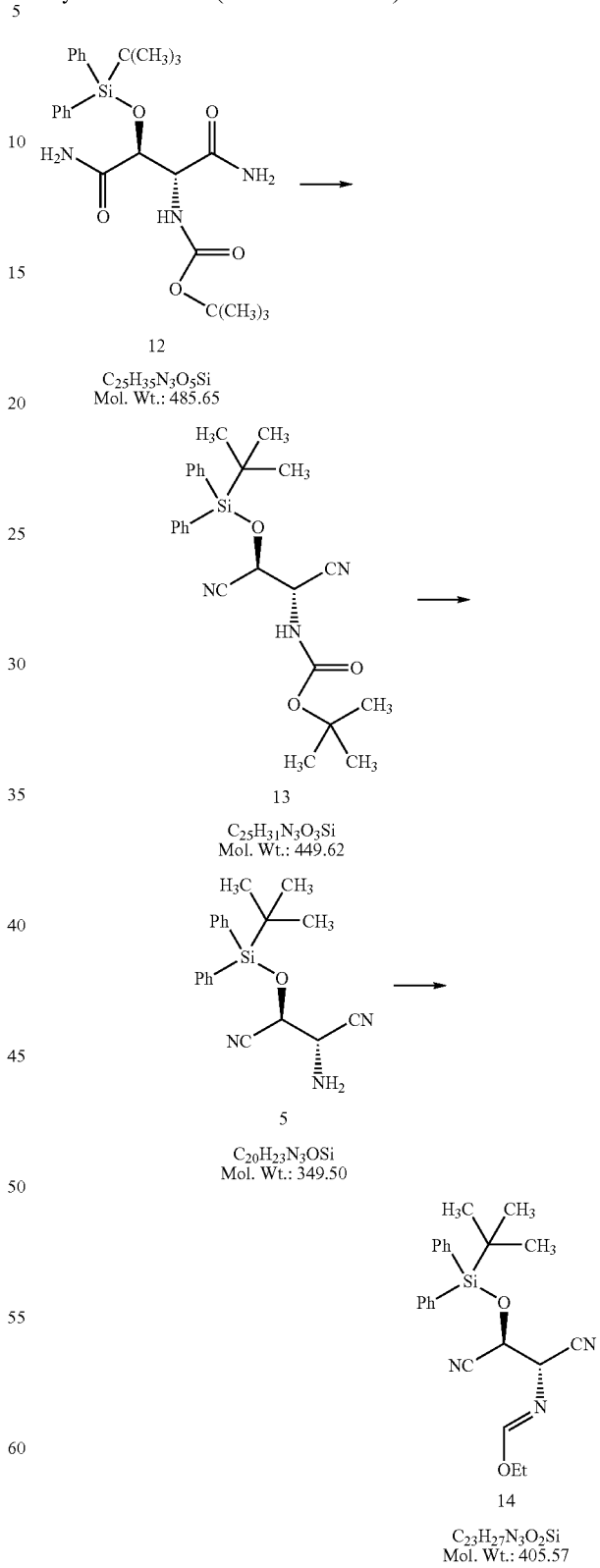

An alternate route to the dinitrile compound (5) is shown below. The diethyl (2S,3S)-2,3-epoxysuccinate ring is opened nucleophilic cleavage of the epoxide by azide and finally the one-pot reduction-protection of the azide group into the N-(tert-butoxycarbonyl) amino group (Saito, S.; K. Komada & T. Moriwake. Org. Synth. 73: 184-200, 1995). Diethyl (2R, 3S)-2-(N-tert-butoxycarbonyl) amino-3-hydroxysuccinate is converted in three steps to the corresponding succinonitrile by the Rappoport procedure. Amino protecting groups are removed under mildly acidic conditions to obtain the compound 5:

The Greenberg method involved acetylation of deoxyribose, followed by azide formation and subsequent reduction: The amino protected deoxyribose according to the Greenberg report was prepared with a yield of 87%. Reduction of the azidosugar was carried out by the sodium hydride in THF with drop-wise addition of methanol as described below: Soai, K.; S. Yokoyama & A. Ookawa. Synthesis, 48-49, 1986. Shown below, the acetylated-1 amino-deoxyribose (betalal-

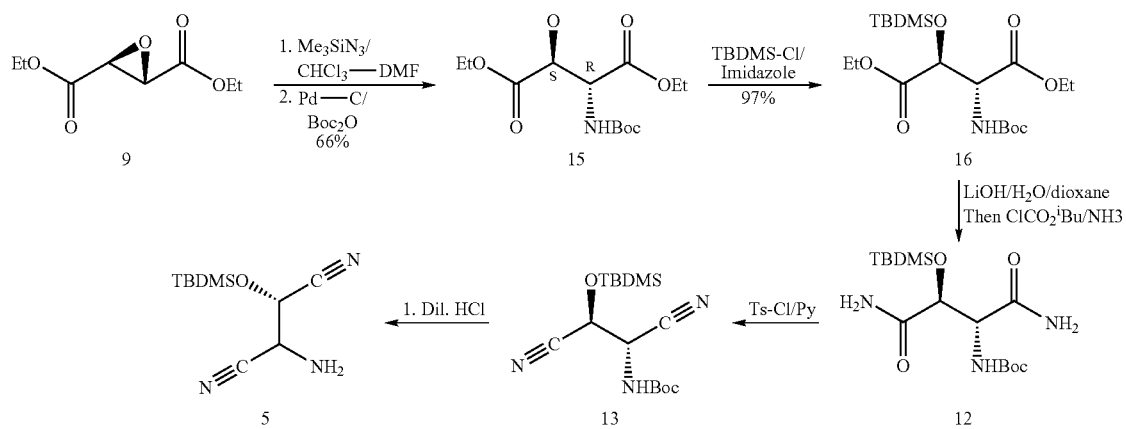

pha ratio of 65/35) is reacted with trimethyl orthoester to give the imino-ether:

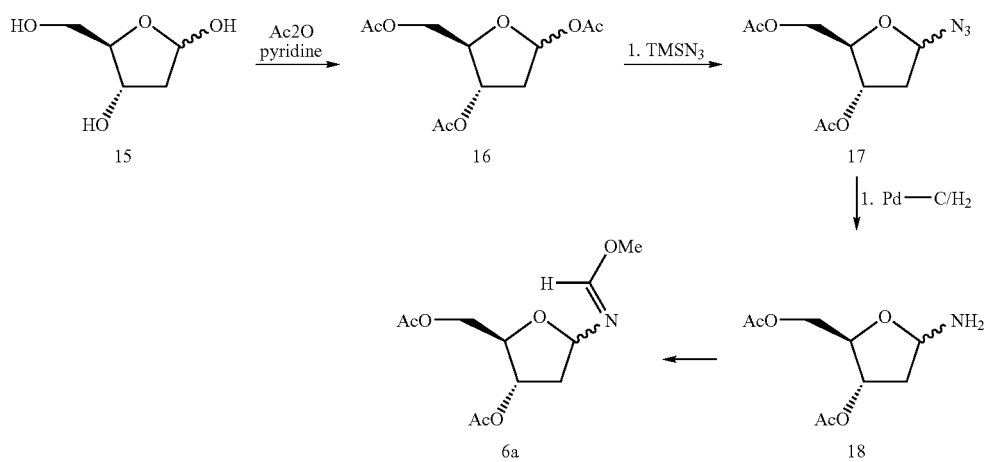

The chiral carbohydrate part of the molecule can be 1'-amino-deoxyribose (6a), which can be produced efficiently on a large scale from deoxyribose in three steps by the method of Greenburg (Haraguchi, K.; M. O. Delaney, C. J. Weiderholt, A. Sambandam, Z. Hantosi & M. Greenberg, J. Am. Chem. Soc. 124: 3263-3269, 2002). 1'-amino-deoxyribose could also be obtained from commercial sources (CMS Chemicals, UK or Berry & Associates, USA). Deoxyribose can be purchased from CMS Chemical Ltd, The Quorum, Oxford OX42JZ, UK (cms-chemicals.com).

In alternative embodiments, different sugars are used in place of deoxyribose. These modified sugars form the carbohydrate portion of the Pentostatin analogs. Sugars contemplated include monosaccharides—pentoses (furanoses) such as arabinose, xylose, ribose, Lyxose or aldohexoses (pyranoses) including glucose, galactose, mannose, gulose, Idose, Talose, Altrose, Allose, and ketohexoses such as fructose, sorbose, and tagatose. In other embodiments non-natural sugar moieties such as thiosugars, azasugars, carbacyclic sugars are used in these processes leading to additional analogs of pentostatin, as shown below:

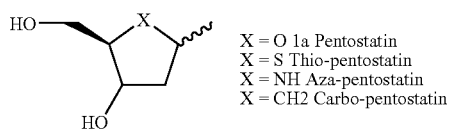

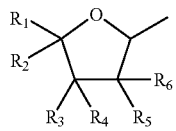

wherein $R_1$, $R_2$, $R_3$, $R_4$, $R_5$, and $R_6$ are independently selected from OH, H, methyl, alkyl, $CH_2OH$, or a halogen; or

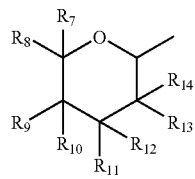

wherein $R_7$, $R_8$, $R_9$, $R_{10}$, $R_{11}$, $R_{12}$, $R_{13}$, and $R_{14}$ are independently selected from OH, H, methyl, alkyl, $CH_2OH$, or a halogen.

Cyclization of dinitrile derivatives with a number of amines was performed to examine the practicality of the formation of the imidazole ring via the nucleophilic addition of an amino group to an electrophilic cyano functionality. These methods were developed using the derivatives shown below. These are simpler analogs showing the successful formation of the 5 (imidazole) and 7 membered rings. The following reaction with the diarninomalononitrile was done as reported (Jose Alves, M.; M. A. Carvalho, M. Fernanda J. R. Proenca & B. L. Booth, J. Heterocyclic Chem. 37: 1041-1048, 2000). The major product was the cyano and amino substituted imidazole derivative. The cyano group in the diaminomalononitrile is more electrophilic than the succinate analogs and also it should be noted that in the above scheme five-versus six-member cyclization is not possible as it is in the succinate reaction.

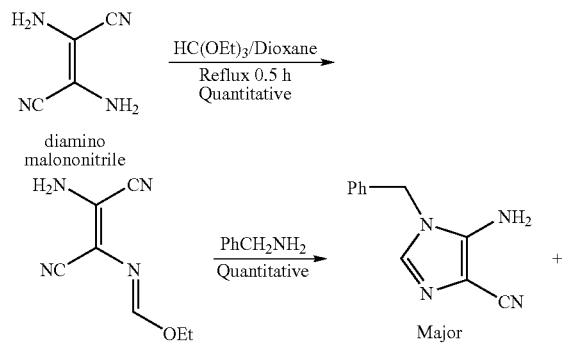

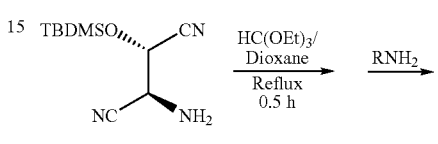

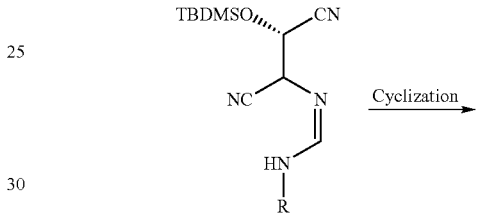

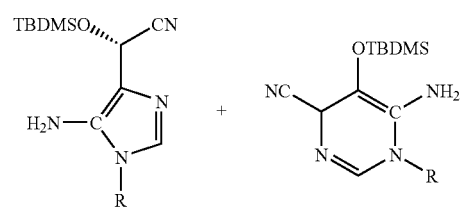

While the cyclization of dinitrile 5 (see above) could theoretically lead to 5- or 6-member heterocycles, experimental investigations indicate that only the 5 membered imidazole was formed. Examples from the Rappoport group and other literature examples suggest that the formation of the 6-membered cyclization is not dominant (Jose Alves, M.; B. L. Booth, A. Carvalho, P. R. Eastwood, L. Nezhat, R. G. Pitchard & M. Femanda J. R. P. Proenca. J. Chem. Soc. Perkin Trans. 2. 1949-1956, 1994).

The reaction of dinitrile 5 with various amines was done to study the cyclization and our ability to remove the N-alkyl group from the imidazole or aglycone. The following reaction of the dinitrile intermediate with benzyl amine shows the formation of the 5 membered imidazole ring system. The free exocyclic amine was first derivatizated to the corresponding imine and the nitrile moiety reduced to the primary amine. This compound was cyclized and the resulting cyclic secondary amine trapped with a benzoyl chloride derivative to give the aglycone (ring system) similar to pentostatin.

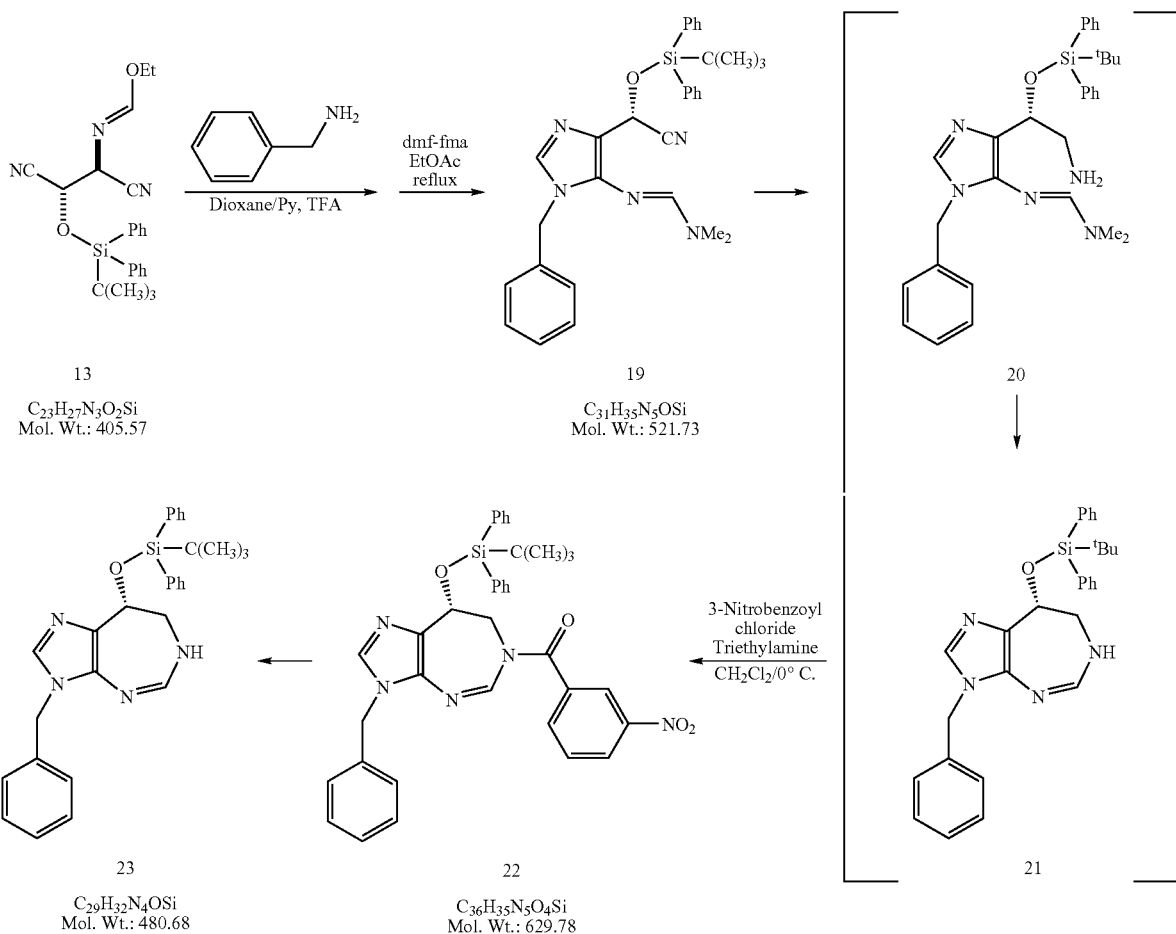
The generality of this approach is illustrated by the following reaction schemes. In the first case an allyl amine is used for the formation of the imidazole ring and subsequent reduction and cyclization and trapping with t-Boc to give the pentostatin ring system.
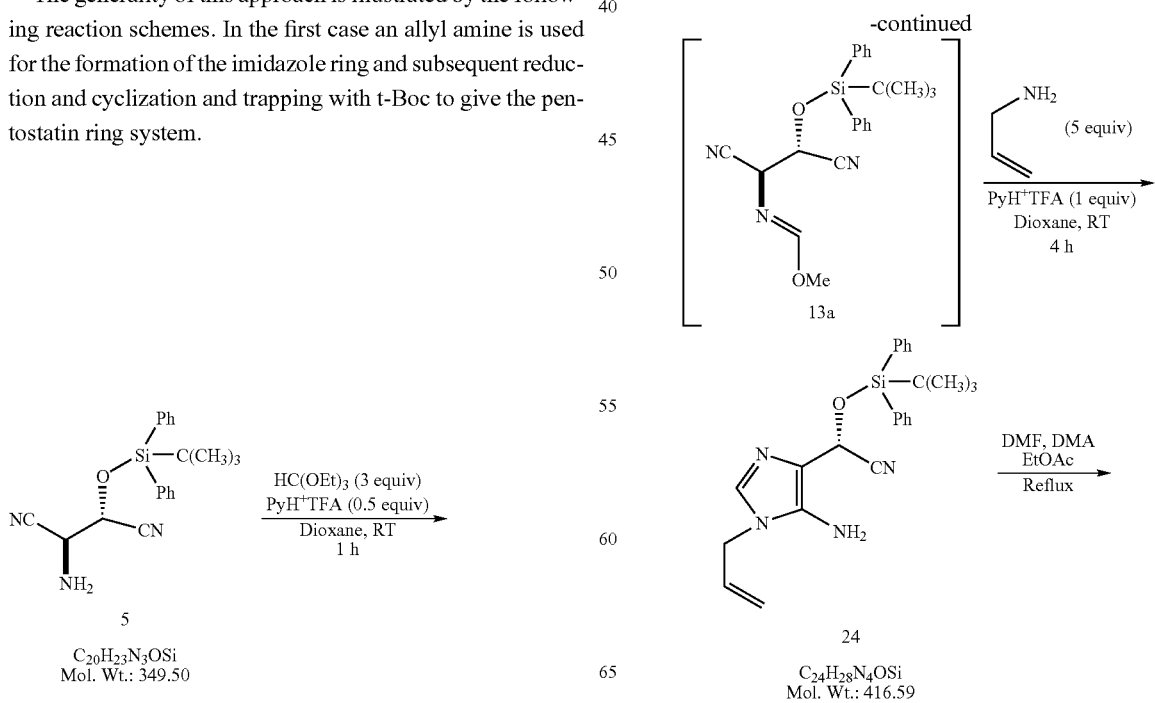

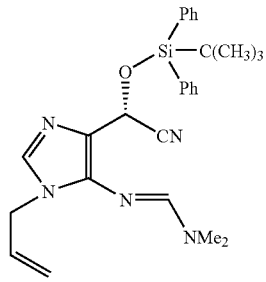
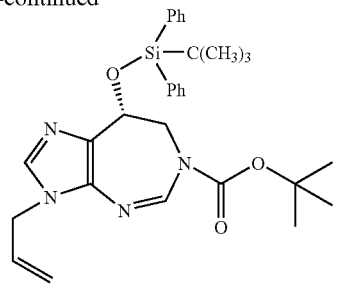
Another example is the use of beta-cyanoethyl amine to form the same aglycone ring system. This is an example of a saturated aliphatic amine that is capable of going through the sequence of transformations to give the aglycone ring system.
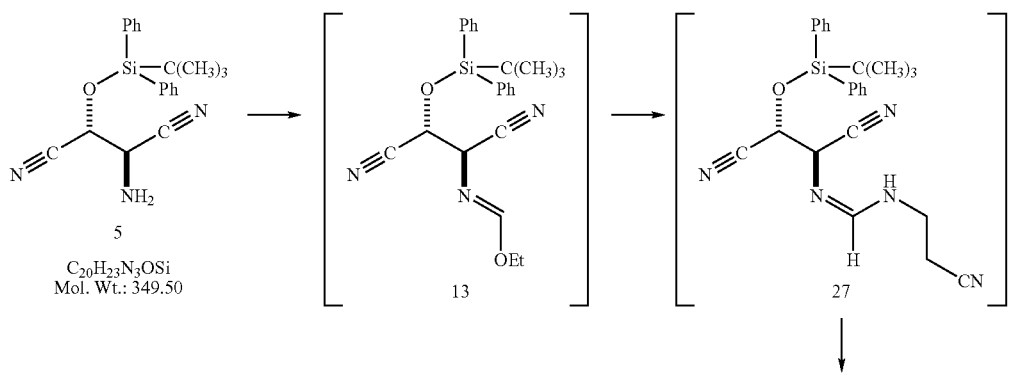
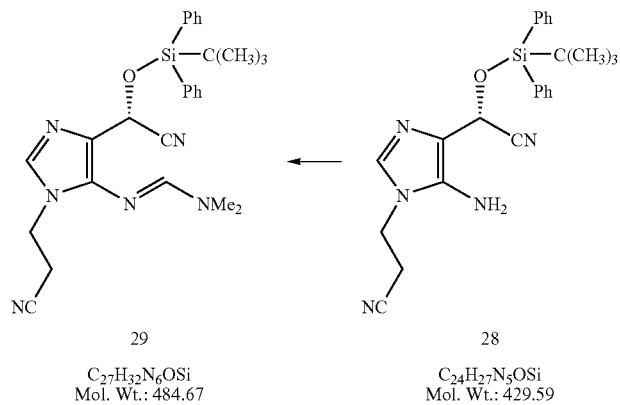

Another example is the use of p-methoxy benzyl amine (another primary amine, R—NH2) to form the aglycone (via the imidazole) after which the p-methoxy benzyl amine moiety can be readily removed to give the protected aglycone suitable for glycosylation to form Pentostatin
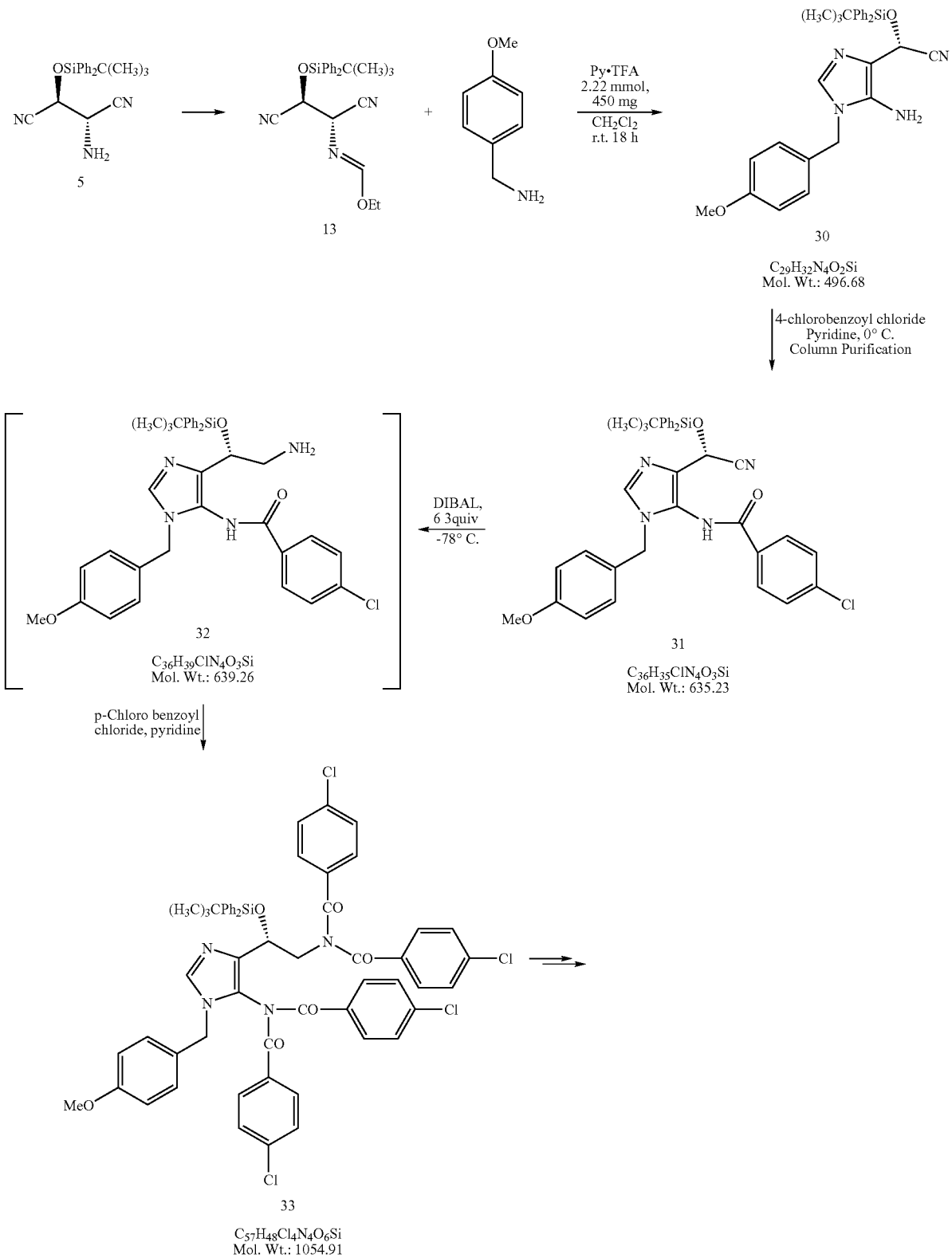

As explained above, the alkyl group of the primary amines which are cyclized with the succinonitrile 5 to form the five-membered imidazole ring can be removed. They can be removed before or after the second cyclization [to give the seven membered ring]. When they are removed after the completion of the second cyclization they form the aglycone analog. The alkyl group on the imidazole nitrogen thus functions as a nitrogen protecting group. Other reagents for forming this nitrogen-containing protecting group in the five-member ring include 4-fluro benzyl chloride, 4-t-butyl benzyl chloride, Trimethyl Acetal chloride, p-methoxy benzyl chloride, and dimethoxy benzyl amine.

Furthermore, the exocylic amine on the imidazole (intremediate 30) can be trapped with carboxylic acid halides or acyl halides (p-Cl-benzoyl chloride). The primary amine (intermediate 32) obtained from the DIBAL-H reduction of the nitrile on the imidazole ring can also be trapped with similar acyl halides. When the free-unprotected amines are cyclized to form the seven member ring they form a secondary amine which a can also be trapped likewise (see multi-step conversion of intermediate 25 to 26). The process allows for the trapping of the sensitive amino group containing intermediates and increasing their stability.

Specific Route to Pentostatin:

The deoxyribose-imino-ether 6a, or derivates thereof mentioned above, and the dinitrile (5) could be coupled in dioxane as solvent and under reflux to form the imidazolyl-nucleoside:

Definitions

As used herein, the term "alkyl" refers to a straight or branched chain alkyl moiety having 1 or more carbon atoms. Typical lower alkyl groups include methyl, ethyl, propyl, isopropyl, butyl, sec-butyl, t-butyl and pentyl. The term "substituted alkyl" refers to substitution of one or more hydrogen atoms of the alkyl moiety with a substituent independently selected from halo, hydroxy, protected hydroxy, amino, protected amino, acyloxy, nitro, carboxy, protected carboxy, carbamyl, aryl, substituted aryl or alkoxy.

As used herein, the term "aryl" means an aromatic carbocyclic ring system having a single radical containing 6 or more carbon atoms. An aryl group may be a fused or polycyclic ring system. Exemplary aryl groups include phenyl and napthyl.

The term "substituted aryl" refers to an aryl group substituted with one, two or three substituents independently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like.

As used herein, the term "heteroaryl" means aromatic monocyclic or fused or polycyclic ring system having at least five ring atoms and a single radical, in which one or more of the atoms in the ring system is other than carbon, for example, nitrogen, oxygen or sulfur.

The term "substituted heteroaryl" refers to a heteroaryl group substituted with one, two or three substituents independently

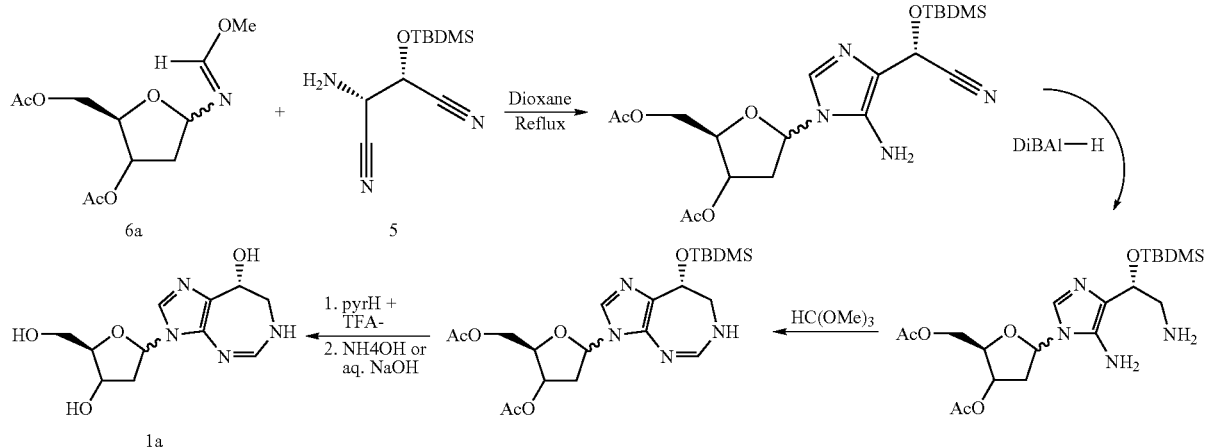

The beta and alpha isomers of 5-amino-ribouranosyl imidazole could then be separated. The nitrile could then be reduced to the primary amine using borane chemistry: The common borane reagent used for this transformation is Dibal-H (diisobutyl aluminum hydride, available from Aldrich) in THF at −78 C. The diamine could also be trapped with acid chlorides to form the diamido derivatives. The diamine may then be reacted with the methylorthoformate [HC(OMe)₃] under mild acid such as pyridinium trifluoroacetic acid to form the seven membered ring. The various protecting groups are removed to give pentostatin or its analogs. The silyl moiety may be deprotected using a number of reagents. Most common reagents are tetrabutyl ammonium fluoride, aqueous HF or Acetic Acid/water/THF. The acetate moieties are removed under basic conditions with aqueous sodium hydroxide.

dently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like.

As used herein, the term "cycloalkyl" refers to a cyclic alkyl group having from 3 or more carbon atoms. Typical cycloalkyl groups include cyclopropyl, cyclopentyl and cyclohexyl. The term "substituted cycloalkyl" refers to substitution of one or more of the hydrogen atoms of the cycloalkyl moiety with a substituent independently selected from halo, hydroxy, protected hydroxy, amino, protected amino, acyloxy, nitro, carboxy, protected carboxy, carbamyl, aryl, substituted aryl or alkoxy.

The term "aralkyl" refers to an alkyl group substituted with an aryl group. Suitable aralkyl groups include benzyl, picolyl, and the like, and may be optionally substituted.

The term "alkenyl" refers to an a straight or branched chain alkenyl moiety having 1 or more carbon atoms bound by at least one double bond.

The term "amine" refers to organic compounds containing a Nitrogen atom.

The term "pentostatin aglycone" refers to the 5:7 ring system nucleobase of pentostatin.

The term "pentostatin analogs" includes pentostatin molecules with a modified sugar moiety, including the sugar modifications set forth herein. The person of ordinary skill will also understand that pentostatin analogs include substitutions along the seven member aglycone ring. The 7-member ring constituents themselves can also be replaced with different constituents. In particular the carbon atom between the two Nitrogen constituents on the seven member ring can be altered based on the orthoester used in cyclization procedure. Further the chirality of the O attached to the seven member aglycone ring can produce stereoisomers, depending on the chirality of the diethyl tartarate starting material.

The term "pentostatin aglycone analog" includes the 5:7 ring system nucleobase of pentostatin with substitutions along the seven member aglycone ring. The 7-member ring constituents themselves can also be replaced with different constituents. In particular the carbon atom between the two Nitrogen constituents on the seven member ring can be altered based on the orthoester used in cyclization procedure. Further the chirality of the O attached to the seven member aglycone ring can produce stereoisomers, depending on the chirality of the diethyl tartarate starting material.

The following non-limiting examples are provided to illustrate the invention. Modifications and variations of the methods and compounds disclosed herein will be apparent to those of ordinary skill in the art, and are intended to be within the scope of the invention.

EXAMPLES

Example 1

Diester-Epoxide 9 (Epoxidation)

Bromotartarate derivative 8 (12 g, 40 mmol) was dissolved in 100 mL dry methanol and cooled down to 0° C. A solution of NaOMe (3 g, 1.4 equiv) in 75 mL dry methanol was prepared and added drop-wise, in 2 h, to the methanolic solution of bromotartarate at 0° C. After completion of addition the reaction mixture was allowed to stir at room temperature for 2 h. TLC (40% and 20% E-H) was used to monitor the reaction. Reaction was incomplete after 2 h. Additional 2 g NaOMe was added at room temperature. TLC showed more than 90% conversion to the higher $R_f$ spot. The excess NaOMe was quenched with acetic acid (10 mL). The reaction mixture was evaporated to dryness and the residue was extracted with $CH_2Cl_2/H_2O$. The organic layer was dried ($Na_2SO_4$) and charged on a silica gel column (Hexanes to 20% E-H).

Yield: 3 g of 9

This reaction was repeated on a 12 g scale and the yield was 4 g. Total yield: 7 g.

Example 2

Diamide-Amine-Alcohol 10

Compound 9, the epoxide (FW 160.12, 7 g, 43.75 mmol) was dissolved in 100 mL methanol and 100 mL of sat. $NH_3$ in MeOH: (~4M solution), ~400 mmol (solubility is 1 g/15 mL). The clear solution was heated in a Parr for 18 h at 70° C. TLC analysis (20% AcOH-MeOH) showed complete conversion. The white precipitate was filtered off and dried in oven. Yield: 85% of 10.

This reaction was repeated 3×: 7 g, 7 g, 10 g. The yields are reproducible. Total Yield: 20 g Example 3

Diamide-t-Boc Derivative 11 (DMF Procedure)

Compound 10 (1.5 g, 10 mmol) was dissolved in 150 mL of dry DMF at 80° C. The compound did not dissolve in DMF at lower temperature. The clear solution was then cooled down to room temperature without any precipitation or cloudiness. To the solution at room temperature was added triethylamine (5 equiv, 50 mmol, 7 mL) and di-tert-butyl carbonate (FW 218.25, d 0.950, 1.5 equiv, 15 mmol, 3.44 mL), and DMAP (120 mg). The mixture was stirred at room temperature 4 h. TLC analysis (20% AcOH-MeOH) showed complete conversion and the appearance of the new non-polar spot (20% M-E). DMF was removed under reduced pressure and the residue was co-evaporated with toluene. The yellow residue was treated with acetone and filtered to remove some yellow insoluble material. Acetone filterate was evaporated and treated with EtOAc. The light-yellow precipitate was filtered. Yield 1.2 g. The mother liquor was charged on a silica gel column (EtOAc to 20% M-E) to separate 150 mg more of the desired product. Total Yield: 1.3 g of 11

Example 4

Protected Diamide 12 (from Compound 11)

Compound 11 (4.2 g, FW 247.27, 17 mmol) was dissolved in 50 mL DMF and Imidazole (3 equiv, 50 mmol, 3.5 g) was added. To the mixture at room temperature was added t-BuPh$_2$Si—Cl (1.8 equiv, 30 mmol, FW 278.86, 7.6 g, 8 mL) was added drop-wise. The mixture was allowed to stir at room temperature overnight. TLC was used to monitor the reaction (20%).

Example 5

Protected Diamide 12: (One-Pot Procedure from Compound 10)

Compound 10 (4.75 g, FW 147.13, 32.28 mmol) was suspended in 100 mL DMF. To the solution was added 1.4 equiv of di-t-butyl carbonate (FW 218.25, d 0.950, 1.4 equiv, 45 mmol, 10 mL). DMAP was not employed. The mixture was stirred at room temperature for 4 h. As the reaction progress the suspension mixture becomes clearer and finally became colorless and clear solution. TLC analysis (20% M-E) showed completion of reaction after 4 h.

To the clear solution was added 5 equiv of imidazole (165 mmol, 11.22 g) followed by 1.5 equivalents of t-butyldimethylsilyl chloride (FW 278.86, 12 g). The reaction mixture was stirred at room temperature overnight. TLC analysis showed complete reaction. DMF was removed under reduced pressure. The residue was extracted with $CH_2Cl_2$/Sat. Aq. $NaHCO_3$. The methylene chloride layer was dried and charged on a silica gel column (80% E-H to 100% E). Yield: 15 g, 98% of 12. This reaction was repeated on a 50 mmol scale. Yield: 21 g (86%)

Example 6

Fully-Protected Succinonitrile (Dinitril) 13

Compound 12 (15 g, FW 485.65, 31 mmol, 1 equiv) was dissolved in 150 mL pyridine and p-toluenesulfonyl chloride (4 equiv, 120 mmol, FW 190.65, 22 g) was added. The mixture was stirred at 60-70° C. overnight. Pyridine was removed under reduced pressure and the residue was co-evaporated with toluene (2×100 mL). The residue was dissolved in 10% E-H and charged on a silica gel column. Yield: 11 g (79%) of 13.

This reaction was repeated on A 41 mmol SCALE. Yield: 15 g.

Example 7

Amine Deprotected Dinitrile 5

To the solution of compound 13 (670 mg, 1.5 mmol) in 25 ml methylene chloride at 0° C. was added 3 equiv TFA. No Reaction was observed. To the mixture was added 2 mL of 10% $H_2SO_4$/Dioxane. The reaction mixture was stirred at 0° C. for 4 h. TLC (20% E-H) showed the completion of the reaction.

Example 8

Amine Deprotected Dinitrile 5

Compound 13 (7.5 g, 16.68 mmol) was dissolved in 10 mL dioxane and at room temperature was added 25 mL of 10% $H_2SO_4$ in dioxane. Reaction mixture was stirred at room temperature for 3 h. The mixture was poured into 100 g ice/100 mL $NH_4OH$. The neutralized solution was extracted with $CH_2Cl_2$. The methylene chloride layer was dried over sodium sulfate and charged on a silica gel column.

Yield: 4 g/69% of 5.

Example 9

Dinitrile-iminoether 14

Compound 5 (4 g, 11.44 mmol) was dissolved in 50 mL dry dioxane and triethyl orthoformate (FW 148.2, d 0.891, 3 equiv, 34 mmol, 5.6 mL) was added. The mixture was heated at 60° C. until a spot for the starting material could be detected (TLC 20% E-H). Yield: 3 g, % 65 of 14.

Example 10

TriAcetyl-deoxy-d-ribose 16 (Acetylation)

D-Deoxyribose 15 (30% $H_2O$, 20 g, FW 134.13, 100 mmol) was co-evaporated with pyridine (3×100 mL) and then dissolved in 100 mL pyridine. At room temperature, was added DMAP (1 g) and drop-wise acetic anhydride (5 equiv, 500 mmol, 47 mL). The reaction mixture was stirred at room temperature overnight. Pyridine was removed on rotavapor and the residue was co-evaporated with toluene (2×100 mL). The residue was extracted with $CH_2Cl_2$/sat. aq. $NaHCO_3$ and the organic layer was separated, dried over sodium sulfate and charged on a silica gel column (10% E-H to 40% E-H). Yield: 31 g of 16. Column: Equill. 20% E-H; 1½ Lit. 20% E-H; 1½ Lit 40%; 2 Lit 50% (Prod was off). TLC (30% E-H).

Example 11

Azido-diacetyl-deoxy-d-ribose 17 (Azidation)

D-Deoxyribose triacetate 16 (100 mmol) was dissolved in 300 mL methylene chloride and the mixture was cooled down to 0° C. To the cold and clear solution was added TMS azide (FW 115.21, d 0.868, 4 equiv, 400 mmol, 53 mL). After 5 min, TMS triflate (FW 222.26, d 1.228, 4equiv, 400 mmol, 73 mL) was added drop-wise. After completion of the reaction (TLC 30% E-H), the reaction mixture was poured into 100 mL sat. Aq. $NaHCO_3$/100 g ice. Methylene chloride layer was separated, dried over sodium sulfate and purified on a silica gel column. 2 L Column:Equillibrated at 20% E_H; Eluted with: 1½ Lit 20% E-H; 1½ Lit 30% E-H; 1½ Lit 40%; 1½ Lit 50%. Yield: 29 g of 17.

Example 12

Amino-diacetyl-deoxy-D-ribose 18 (Reduction)

5 g of the Azido-sugar 17 was dissolved in 100 mL methanol and treated at room temperature with 1.5 g of $NaBH_4$ for 2 h. TLC showed complete conversion to a lower spot product. After disappearance of the SM, the reaction mixture was quenched with 10 mL of 1N HCl. The mixture was evaporated to dryness and the residue was extracted ($H_2O$/$CH_2Cl_2$). The aqueous layer was charged on a XUS column and the product was eluted with 20-40% ACN-$H_2O$. Silica gel column also has been used to separate larger amount of amino sugar 18.

Example 13

Dmf-Protected N-benzyl imidazole (19)

Dinitrile derivative 13, 3 g, 7.4 mmol, was dissolved in 100 mL of dry dioxane and benzyl amine (FW 107.16, d 0.981, 1.8 equiv, 13.5 mmol, 1.5 mL) was added at room temperature. To the mixture then was added 100 mg of pyridinium trifluoroacetate. The mixture was stirred at 50° C. for 4 h. TLC was used to monitor the reaction. The reaction mixture was evaporated and then extracted. EtOAc layer was dried and immediately charged on a silica gel column (charged as 20% E-H, and eluted with 20-505 E-H). The product and the reaction mixture is light sensitive and become dark very quickly! The Yield of the imidazole is only 50% may be due to air oxidation on column.

The exocylic amine on the imidazole was protected by refluxing with dimethylformamide-dimethylacetal in ethtlacetate to give compound 19

Example 14

Cyclization of 19

DMF protected N-benzyl imidazole 19 (710 mg, FW 521.73, 1.3 mmol) was dissolved in 10 ml methylene chloride and 5 mmol (4 equiv) of 1.0M solution of DIBAH in THF (5 m) was added drop-wise at −40° C. TLC was used to monitor progress of the reaction (40% E-H). Complete disappearance of the starting material to a base-line spot was observed upon completion of the addition. Reaction mixture was stirred at room temperature overnight. Work-up: To the reaction mixture was poured into ice-1N HCl (50 mL). The resulting solution was extracted with EtOAc (2×15 mL). The aqueous layer was neutralized at 0° C. with 5N NaOH. The mixture was thoroughly extracted with EtOAc (2×15 mL). The EtOAc layer was dried over sodium sulfate and evaporated to dryness. The residue was co-evaporated with toluene (2×15 mL). The residue (cpd 20) was dissolved in dioxane and reflux for 1 h. The mixture was cooled and at 0° C. was added 50 mmol triethylamine (7 mL) and 2.7 equiv of 3-nitrobenzoyl chloride (FW 185.57, 500 mg). The mixture was stirred at 0° C. and allowed to warm-up to room temperature overnight. The reaction mixture was extracted with sat. aq. $NaHCO_3$. The organic layer was separated, dried over sodium sulfate, and evaporated to dryness. The residue was dissolved in 20% E-H and charged on a silica gel column to separate 300 mg of the desired product. Yield 35% of 22.

Example 15

N-Benzyl-O-silyl-Aglycone 23

3-Nitrobenzoyl derivative 22 (300 mg) was dissolved in dioxane and treated with Conc. NH4OH and heated in a sealed Parr at 55° C. for 8 h. Reaction mixture was evaporated to dryness and the residue was extracted (EtOAc) and charged on a silica gel column. The most polar fraction (Rf 0.6 in EtOAc) proved to be the desired product. Yield 85% of the protected aglycone 23.

Example 16

N-allyl-imidazole (24)

Dinitrile-amine derivative (5), (450 mg, 1.28 mmol) was dissolved in 15 ml dry dioxane and triethyl orthoformate (3 equiv, 3.86 mmol, 1 mmol~166 μL, 640 μL) was added. To the solution pyridinium trifluoroacetate (0.5 equiv, 0.64 mmol, FW 193.13, 123 mg) was added at room temperature. The reaction mixture was stirred at room temperature for 1 h (till no spot for the starting material can be detected). This results in the formation of iminomethyletherdinitrile 13a Then allyamine (5 equiv, 6.4 mmol, FW 57.09, d 0.763, 480 μL) was added. To the solution during 4 hours, four times was added total of 2 equiv of pyridinium trifluoroacetate (500 mg, each time 125 mg). TLC analysis of the reaction mixture showed completion of reaction. The reaction mixture was diluted with 30 mL EtOAc and 20 mL of aq. $NaHCO_3$. The organic layer was chromatographed (20% E-H to 40% E-H) to afford 150 mg of the desired product N-allyl-imidazole derivative(24).

Example 17

N-Allyl-N-t-butoxycarbonyl-O-silyl-imidazole 26

N-allyl-imidazole derivative 24 (150 mg) was dissolved in 10 mL ethyl acetate and DMF. DMA (excess, 1 mL) was added and the mixture was reflux for 30 min. TLC showed complete disappearance of the starting material and the appearances of a higher Rf product the Dmf-protected-N-allyl-imidazole (25).

The above reaction mixture was evaporated to dryness and re-dissolved in 10 ml dioxane. The mixture was cooled down to 0° C. and 1 mL of DIBAL (1 M solution in THF, 1 mmol, ~3 equiv) was added and the mixture was allowed to stir and warm-up to room temperature overnight. WORK-UP: The reaction mixture was quenched with 10 mL 1N HCl and the mixture was extracted with EtOAc. The aqueous layer was brought to pH 10 by addition of 5N NaOH and the mixture was extracted with EtOAc to give the aglycone. t-BOC Reaction: The EtOAc layer containing the aglycone was dried and evaporated. The residue was treated with Di t-butylcarbonate in EtOAc. After 30 min reflux the mixture was evaporated and charged on a silica gel column (20% E-H) to separate the desired product N-Allyl-N-t-butoxycarbonyl-O-silyl-imidazole 26, as judged by its $^1$H NMR spectrum.

Example 18

-N-dmf-N-(2-cyanoethyl)-imidazole derivative (29)

α-Aminodinitrile (5) (1.7 g, 4.8 mmol, 1 equiv) was dissolved in 10 mL triethyl orthoformate (excess) and reflux for 2 h. Excess triethyl orthoformate was removed under reduced pressure and to the residue was added 25 mL acetonitrile and 1.8 equiv, 8.75 mmol, 1.1 g of 3-aminopropylnitrile fumarate (FW 129.13). The reaction mixture was kept at room temperature overnight. Overnight the reaction became dark and clear, the mixture was quenched with $NaHCO_3$ and extracted with EtOAc. The EtOAc layer was dried over sodium sulfate and the treated with dmf-dma (5 eq) and heated to 60 C for 4-5 hours. The reaction mixture was extracted and purified on a silica gel column (40%-100% EtOAc/Hexanes). Yield: 100 mg, 200 mg & 450 mg (28 from reactions starting with (700 mg, 1 g & 3 g) of 5

Example 20

Synthesis of 31 t-Boc derivative 12 (10 g, 22.24 mmol) was treated with 10% H2SO4/Dioxane (3.6M, 35 mL) and stirred at room temperature for 2 h (till TLC shows the completion of the reaction). The reaction mixture was poured into 50 g ice and 50 mL of concentrated NH4OH. The mixture was extracted with EtOAc and the organic layer was dried over sodium sulfate, filtered and evaporated to dryness. The residue was co-evaporated with toluene (2×50 mL). The residue (dinitrile 5)was then reflux for 45 min with 35 mL of triethyl orthoformate. The mixture was evaporated to dryness to give crude ethyl iminoether derivative 13 and then dissolved in CH2Cl2 (100 mL) and treated with pyridinium trifluoroacetate (2.22 mmol, 450 mg) and p-methoxybenzyl amine (22.24 mmol, 2.8 mL) overnight at room temperature and in dark (covered by aluminum foil). Next day the reaction mixture (containing intermediate 30) was place in an ice-bath and pyridine (10 mL) was added. To the cold reaction mixture then was added drop-wise p-chlorobenzoyl chloride (0.8 equiv, 17.8 mmol, 2.25 mL). The reaction mixture stirred at 0° C. for 2 h and the evaporated to dryness, and co-evaporated with toluene (2×50 mL). The residue was extracted withy EtOAc and the organic layer was separated, dried (NaSO4), evaporated and purified on a silica gel column. Yield (4 steps): 5.6 g, 40% of 31

Example 21

Synthesis of 32, 33

DIBAH: 6 equiv (400 mg scale in 40 ml THF, 0.66 mmol, 4 mL 1M), −78° C., Pyridine: 40 mL at −78° C., p-ClBz Chloride 3 equiv, 2 mmol. DIBAL reaction was allowed to slowly warm-up to R.T. overnight. Next day, the mixture was evaporated to dryness. TLC examination (40% and 60% E-H) showed three spots. HPLC examination of the reaction mixture showed three peaks. Chromatography separation yielded two products, each of about 100 mg. $^1$H NMR of both products (SN 518A and SN518B) were consistent with fully protected desired product. LCMS examination will be performed. This reaction will be repeated on scale of 1 g result was the same 500 mg of the per-benzoylated product (see the experiment below).

(Dec. 3, 2003):1 g, 1.6 mmol, DIBAH, 10 mL, 6 equiv. 4-ClBzCl, 2 equiv, 3.2 mmol. Reaction was allowed to warm-up slowly to room temperature overnight. Extraction with sat. aq. NaHCO3 caused gelatin-like precipitation that was filtered through hiFlo. Extraction and silica gel column produced two fractions.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description. Patents, patent applications, publications, product descriptions, and protocols are cited throughout this application, the disclosures of which are incorporated herein by reference in their entireties for all purposes.

What is claimed:

1. A method for synthesizing pentostatin, a pentostatin analog, pentostatin aglycone, or a pentostatin aglycone analog which method comprises the steps of:

converting a dialkyl tartarate to a succinonitrile derivative having the formula:

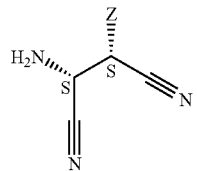

wherein Z is $OR_{15}$, wherein $R_{15}$ is a protecting group;

reacting the succinonitrile derivative with an iminoether selected from:

(a) an iminoether having the formula

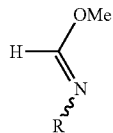

wherein R is a protecting group or

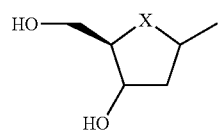

wherein X is O, S, NH, or $CH_2$; or (b) an iminoether having the formula

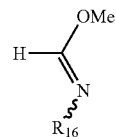

wherein $R_{16}$ is

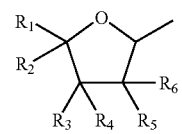

wherein $R_1$, $R_2$, $R_3$, $R_4$, $R_5$, and $R_6$ are independently selected from OH, H, methyl, alkyl, $CH_2OH$, a halogen, a substituted or unsubstituted O—R' group, a substituted or unsubstituted S—R' group, or a NR'R" group, wherein R' and R" are independently a straight-chained or substituted alkyl or alkenyl group; or (c) an iminoether having the formula

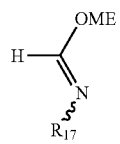

wherein $R_{17}$ is

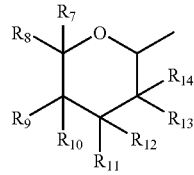

wherein $R_7$, $R_8$, $R_9$, $R_{10}$, $R_{11}$, $R_{12}$, $R_{13}$, and $R_{14}$ are independently selected from OH, H, methyl, alkyl, $CH_2OH$, a halogen, a substituted or unsubstituted O—R''' group, a substituted or unsubstituted S—R''' group, or a NR'''R'''' group, wherein R''' or R'''' are independently a straight-chained or substituted alkyl or alkenyl group;

to form a imidazole ring compound, wherein the imidazole ring compound comprises a moiety having a cyano group;

reducing the cyano group on the imidazole ring compound to a primary amino group;

cyclizing the primary amino group with a second amino group on the imidazole ring compound; and removing any protecting groups to obtain pentostatin, pentostatin aglycone, a pentostatin compound, wherein the pentostatin compound is selected from:

(a) a pentostatin analog in which the oxygen atom in the sugar moiety is replaced with a sulfur atom, a NH group, or a $CH_2$ group;

(b) a pentostatin analog in which the sugar moiety is based on arabinose, xylose, ribose, lyxose glucose, galactose, manose, gulose, idose, talose, altrose, allose, fructose, sorbose or tagatose instead of deoxyribose; and (c) a pentostation aglycone analog which does not contain a sugar moiety, and wherein the carbon atom between the two nitrogen atoms on the seven-member ring is altered.

2. The method of claim 1, wherein the dialkyl tartarate is in either the L or D enantiomeric form.

3. The method of claim 2, wherein the dialkyl tartarate is L-Diethyl tartarate.

4. The method of claim 2, wherein the dialkyl tartarate is D-Diethyl tartarate.

5. The method of claim 1, wherein the iminoether is obtained from a reaction of ammonia or primary amine with a trimethyl orthoester.

6. The method of claim 5, wherein the primary amine has the formula $R_{21}$—$NH_2$, wherein $R_{21}$ is a substituted or unsubstituted alkyl group, a substituted or unsubstituted alkenyl group, a substituted or unsubstituted aryl group, a substituted or unsubstituted aralkyl group, a substituted or unsubstituted cycloalkyl group, a substituted or unsubstituted alkoxyalkyl group, or a substituted or unsubstituted heteroaryl group.

7. The method of claim 6, wherein the primary amine is benzyl amine, allyl amine, beta-cyanoethyl amine, or p-methoxy benzyl amine.

8. The method of claim 1, wherein the iminoether has the formula

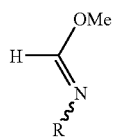

wherein R is deoxyribose, ribose, arabinose, xylose, ribose, lyxose, glucose, galactose, mannose, gulose, idose, talose, altrose, allose, fructose, sorbose, or tagatose.

9. The method of claim 8, wherein R is deoxyribose, the dialkyl tartarate is L-diethyl tartarate, and pentostatin is synthesized.

10. The method of claim 1, wherein the iminoether has the formula

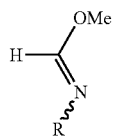

wherein R is

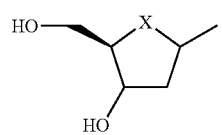

wherein X is O, S, NH, or $CH_2$; or

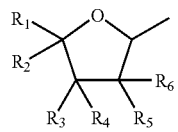

wherein $R_1$, $R_2$, $R_3$, $R_4$, $R_5$, and $R_6$ are independently selected from OH, H, methyl, alkyl, $CH_2OH$, a halogen, a substituted or unsubstituted O—R' group, a substituted or unsubstituted S—R' group, or a NR'R" group, wherein R' and R" are independently a straight-chained or substituted alkyl or alkenyl group; or

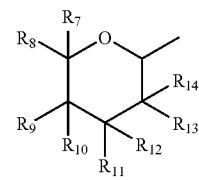

wherein $R_7$, $R_8$, $R_9$, $R_{10}$, $R_{11}$, $R_{12}$, $R_{13}$, and $R_{14}$ are independently selected from OH, H, methyl, alkyl, $CH_2OH$, a halogen, a substituted or unsubstituted O—R''' group, a substituted or unsubstituted S—R''' group, or a NR'''R'''' group, wherein R''' or R'''' are independently a straight-chained or substituted alkyl or alkenyl group.

11. The method of claim 1, wherein the cyclization is performed with an orthoformate.

12. The method of claim 11, wherein the orthoformate has the formula $HC(OR_{18})_3$, wherein $R_{18}$ is a straight-chained or substituted alkyl group.

13. The method of claim 1, further comprising the step of glycosylating the pentostatin aglycone or the pentostatin aglycone analog.

14. The method of claim 13, wherein the pentostatin aglycone is glycosylated with deoxyribose to obtain pentostatin.

15. The method of claim 1, wherein $R_{15}$ is TBDMS, $SiPh_2C(CH_3)_3$, an acetyl group, dimethoxytrityl, or Methylthioethyl amine.

16. The method of claim 1, wherein the primary amino group comprises a protecting group, and the protecting group is removed after cyclization.

17. A method for synthesizing pentostatin or a pentostatin analog, which method comprises the steps of:

converting a L diethyl tartrate to a succinonitrile intermediate, the intermediate having the formula:

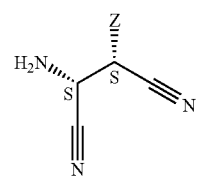

wherein Z is $OR_{19}$, wherein $R_{19}$ is a protecting group;

reacting the succinonitrile intermediate with an amino sugar intermediate having the formula:

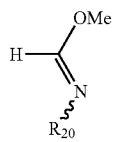

wherein $R_{20}$ is

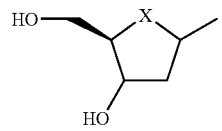

wherein X is O, S, NH, or $CH_2$; or wherein $R_{20}$ is

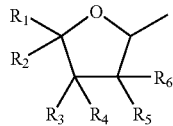

wherein $R_1$, $R_2$, $R_3$, $R_4$, $R_5$, and $R_6$ are independently selected from OH, H, methyl, alkyl, $CH_2OH$, or a halogen; or wherein $R_{20}$ is

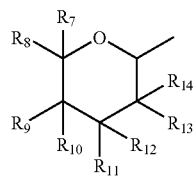

wherein $R_7$, $R_8$, $R_9$, $R_{10}$, $R_{11}$, $R_{12}$, $R_{13}$, and $R_{14}$ are independently selected from OH, H, methyl, alkyl, $CH_2OH$, or a halogen, to form a imidazole ring compound, wherein the imidazole ring compound comprises a moiety having a cyano group;

reducing the cyano group on the imidazole ring compound to a primary amino group; and adding a orthoformate to cyclize the primary amino group with a second amino group on the imidazole ring compound; and removing the protecting group to obtain pentostatin or the pentostatin compound, wherein the pentostatin compound is selected from:

(a) a pentostatin analog in which the oxygen atom in the sugar moiety is replaced with a sulfur atom, a NH group, or a $CH_2$ group; and (b) a pentostatin analog in which the sugar moiety is based on arabinose, xylose, ribose, lyxose glucose, galactose, manose, gulose, idose, talose, altrose, allose, fructose, sorbose or tagatose instead of deoxyribose.

18. The method of claim 17, wherein the amino sugar intermediate has the formula

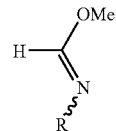

wherein R is deoxyribose, ribose, arabinose, xylose, ribose, lyxose, glucose, galactose, mannose, gulose, idose, talose, altrose, allose, fructose, sorbose, or tagatose.

19. The method of claim 18, wherein R is deoxyribose.

20. The method of claim 17 wherein R is

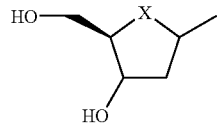

wherein X is S, NH, or $CH_2$.

* * * * *